US011224686B2

(12) United States Patent
Liang et al.

(10) Patent No.: US 11,224,686 B2
(45) Date of Patent: Jan. 18, 2022

(54) FILTER MATERIAL AND MANUFACTURING METHOD THEREOF

(71) Applicant: Sangtech Lab Inc., Taipei (TW)

(72) Inventors: Cheng-Sheng Liang, Taipei (TW); Po-Ju Lin, Taipei (TW); Yu-Ping Chen, Taipei (TW); Chun-Hung Chen, Taipei (TW); Pei-Chieh Chuang, Taipei (TW)

(73) Assignee: Sangtech Lab Inc., Taipei (TW)

( * ) Notice: Subject to any disclaimer, the term of this patent is extended or adjusted under 35 U.S.C. 154(b) by 164 days.

(21) Appl. No.: 16/664,953

(22) Filed: Oct. 28, 2019

(65) Prior Publication Data

US 2020/0237996 A1    Jul. 30, 2020

Related U.S. Application Data

(60) Provisional application No. 62/797,888, filed on Jan. 28, 2019.

(51) Int. Cl.
  *A61M 1/36*    (2006.01)
  *B01D 39/16*    (2006.01)

(52) U.S. Cl.
  CPC ....... *A61M 1/3633* (2013.01); *B01D 39/1623* (2013.01); *A61M 2202/0439* (2013.01)

(58) Field of Classification Search
  CPC .......... B01D 2323/04; B01D 2323/225; B01D 67/0088; C08J 2327/18; C08J 7/0427; Y02P 20/54; A61M 2202/0429; A61M 2202/0439; A61M 2202/0035; A61M 2202/0042
  See application file for complete search history.

(56) References Cited

U.S. PATENT DOCUMENTS

| 4,302,334 | A | * | 11/1981 | Jakabhazy | ............. | B01D 71/38 |
| | | | | | | 210/500.41 |
| 4,925,572 | A | | 5/1990 | Pall | | |
| 4,976,861 | A | | 12/1990 | Pall | | |
| 5,783,094 | A | | 7/1998 | Kraus et al. | | |
| 6,251,276 | B1 | * | 6/2001 | Motomura | .......... | A61M 1/3633 |
| | | | | | | 210/490 |
| 7,037,642 | B2 | | 5/2006 | Hei | | |
| 7,410,066 | B2 | | 8/2008 | Yamada et al. | | |
| 7,775,376 | B2 | | 8/2010 | Bonaguidi et al. | | |
| 8,136,676 | B2 | * | 3/2012 | Mizomoto | ............ | C08F 220/28 |
| | | | | | | 210/508 |
| 8,528,746 | B2 | * | 9/2013 | Kim | ....................... | B01D 71/68 |
| | | | | | | 210/500.35 |
| 8,961,789 | B2 | * | 2/2015 | Watkins | .................. | A61M 1/26 |
| | | | | | | 210/321.68 |
| 9,585,997 | B2 | | 3/2017 | Suzuki et al. | | |
| 9,623,352 | B2 | * | 4/2017 | Kas | ......................... | C12N 7/00 |
| 9,963,352 | B2 | * | 5/2018 | Aranda | .................... | C01B 32/60 |
| 2003/0225439 | A1 | * | 12/2003 | Cook | ........................ | A61F 2/82 |
| | | | | | | 607/2 |
| 2004/0059717 | A1 | | 3/2004 | Klare et al. | | |
| 2008/0017577 | A1 | * | 1/2008 | Yi | ....................... | B01L 3/50825 |
| | | | | | | 210/645 |
| 2011/0253621 | A1 | | 10/2011 | Kim et al. | | |
| 2012/0118816 | A1 | * | 5/2012 | Gjoka | .................... | B01D 71/32 |
| | | | | | | 210/506 |
| 2013/0137784 | A1 | * | 5/2013 | Krause | ............... | B01D 67/0011 |
| | | | | | | 521/27 |
| 2014/0291227 | A1 | | 10/2014 | Ducoroy et al. | | |

FOREIGN PATENT DOCUMENTS

| CN | 1856332 | 11/2006 |
| CN | 100475307 | 4/2009 |
| CN | 103272493 | 9/2013 |
| CN | 105153349 | 12/2015 |
| CN | 105642132 | 6/2016 |
| CN | 105813663 | 7/2016 |
| CN | 107138058 | 9/2017 |
| EP | 1018346 | 7/2000 |
| JP | 2000197814 | 7/2000 |
| JP | 2001226874 | 8/2001 |
| JP | 2006500438 | 1/2006 |
| JP | 2008045077 | 2/2008 |
| KR | 20050057446 | 6/2005 |
| KR | 20110115856 | 10/2011 |
| TW | I627991 | 7/2018 |
| WO | 8903717 | 5/1989 |

OTHER PUBLICATIONS

"Office Action of Taiwan Counterpart Application", dated Apr. 7, 2020, p. 1-p. 3.
"Search Report of Europe Counterpart Application", dated Mar. 5, 2020, p. 1-p. 7.
"Office Action of Japan Counterpart Application", dated Dec. 15, 2020, p. 1-p. 3.
"Office Action of China Counterpart Application" with English translation thereof, dated Jun. 2, 2021, p. 1-p. 29.
"Office Action of Korea Counterpart Application" with English translation thereof, dated Jul. 27, 2021, p. 1 -p. 11.

* cited by examiner

*Primary Examiner* — Ana M Fortuna
(74) *Attorney, Agent, or Firm* — JCIP Global Inc.

(57) ABSTRACT

A filter material and a manufacturing method thereof are provided. The manufacturing method includes hydrophilizing the filter material by supercritical fluid processing technology, so as to filter out white blood cells in the blood.

6 Claims, No Drawings

FILTER MATERIAL AND MANUFACTURING METHOD THEREOF

CROSS-REFERENCE TO RELATED APPLICATION

This application claims the priority benefit of U.S. provisional Patent application No. 62/797,888, filed on Jan. 28, 2019. The entirety of the above-mentioned patent application is hereby incorporated by reference herein and made a part of this specification.

BACKGROUND

Technical Field

The invention is related to a filter material and a manufacturing method thereof, and more particularly, to a filter material manufactured by supercritical fluid processing technology and a manufacturing method thereof.

Description of Related Art

In traditional medicine, as regards the medical treatment of blood transfusions, whole blood or blood components are mainly transferred to patients. Due to the research and clinical data accumulated over time, the medical treatment of blood transfusions has been significantly improved. In the current blood transfusion medical treatment, whole blood transfusion becomes less common. Instead, concentrated red blood cells are transferred to patients who need red blood cells, and platelet concentrate is transferred to patients who need platelets. These blood cell components are separated from the whole blood through centrifugation method. In addition to the components listed above, whole blood also contains white blood cells, which provide protection mechanism against bacterial and viral infections.

In recent years, in the medical treatment field of blood transfusion, white blood cells in blood products are usually removed in advance, so as to perform blood transfusion treatment without white blood cells. The reason is that, when blood products containing white blood cells are used for blood transfusion, it may cause adverse side effects, such as headache, nausea, chills, and anhemolytic exothermic reaction, and it may also cause other severe side effects, such as alloantigen sensitization, post-blood transfusion graft-versus-host disease (GVHD) after blood transfusion, and virus infection. The main methods used to remove white blood cells from blood products include the centrifugal separation method and the filter method. The centrifugal separation method utilizes the specific weight difference of blood components. The filter method uses a fibrous material or a porous material having continuous pores as a filter material. The filter method using the filter material is more popular due to advantages such as higher leukocyte removing capability, simple procedure, lower costs, and the like. Therefore, there is a desire for a leukocyte removal filter possessing more excellent leukocyte removing capability that can prevent the above-mentioned heavy side effects.

To improve the leukocyte removal capability of a leukocyte removal filter, both physical factors and chemical factors of the filter must be taken into consideration to have hydrophilic modification for the filter material used. Specifically, as for the filter material for filtering out white blood cells, the filter material is usually hydrophilized, so that blood can pass through the membrane material, and the filtering effect is then achieved through selectivity (affinity) between the filter material and white blood cells. In the prior art, the filter material is a thermally sprayed base material, which is usually hydrophilized through grafting method or coating method. Examples of the method for coating the polymer onto the filter material include a method of dipping the filter material with a polymer solution, a method of spraying the polymer solution to the filter material, and a method of applying or transcribing the polymer solution to the filter material using a photogravure roll or the like.

WO 89/03717 discloses a filter using a porous web with a critical wetting surface tension (CWST) of 53-90 dyn/cm produced by grafting 2-hydroxyethyl methacrylate (HEMA) with methyl acrylate (MA) or methyl methacrylate (MMA) and changing their proportion. U.S. Pat. No. 4,925,572A discloses a filter can have fibers which have been surface modified by exposure to an energy source while in contact with a monomer containing at least one hydroxyl moiety and one moiety capable of activation by an energy source, together with a monomer containing at least one hydrophobic moiety and one moiety capable of activation by an energy source. Thus, product comprising at least one element in which a fibrous medium has been radiation grafted to obtain a critical wetting surface tension. Japan Patent Application No. 2000-197814 discloses a hydrophilic coating material containing quaternary ammonium salt. The use of a quaternary ammonium salt remarkably promoted hydrophilic properties and the CWST of the filter technically exceeded the level achieved by WO89/03717 (Published Japanese Translation of PCT Application No. 3-502094), the method requires a washing step after the coating step to reduce elution. US 20140291227A1 discloses a preparation method of coating polymer and solution which solubilizes polymer and copolymer in ethanol. U.S. Pat. No. 77,753,796 uses an acetonic solution to solubilize the polymer. U.S. Pat. No. 7,410,066B2 uses ethanol in the synthesis of polymer, and the polymer is dissolved in a mixed solvent of isopropanol during the preparation of filter material. U.S. Pat. No. 4,976,861 discloses that grafting is accomplished by compounds containing an ethylenically unsaturated group.

However, whether it is a grafting method or a coating method, a large amount of solvent (e.g., ethanol) must be used to dissolve the hydrophilic monomer or the hydrophilic polymer, and considerable wastewater treatment costs are incurred as a result. Further, after the filter material is hydrophilized through the conventional coating method, fiber properties of the filter material may be changed (e.g., fiber becomes thicker and a pore diameter of the filter material reduces), and operational time is thus affected.

Based on the above, development of a filter material for filtering out white blood cells in the blood and a manufacturing method thereof, which can solve the problems of solvent recovery and wastewater treatment, is an important issue.

SUMMARY

The invention provides a filter material and a manufacturing method thereof configured to filter out white blood cells in the blood, and the filter material is hydrophilized through supercritical fluid processing technology, so that the problems of solvent recovery and wastewater treatment can be effectively solved.

A manufacturing method of a filter material provided by the invention includes hydrophilizing the filter material through a supercritical fluid processing technology, so as to filter out white blood cells in the blood.

In an embodiment of the disclosure, the filter material includes a polyester compound base material.

In an embodiment of the disclosure, the process of hydrophilizing the filter material by using the supercritical fluid processing technology includes the following steps. The filter material is placed in a cylinder and a hydrophilic agent is added. Carbon dioxide gas is poured into the cylinder, a heating reaction is performed to the cylinder, and a pressure of the cylinder is increased. A temperature and the pressure of the cylinder are lowered after the heating reaction is over, and the filter material is taken out.

In an embodiment of the disclosure, the hydrophilic agent is added in an amount of 0.1 wt % to 10 wt % based on a total weight of the filter material.

In an embodiment of the disclosure, a bath ratio obtained by a weight of the filter material divided by a volume of the cylinder is 0.01 to 1.

In an embodiment of the disclosure, the pressure of the cylinder is 70 bar to 500 bar when the heating reaction is performed.

In an embodiment of the disclosure, a temperature of the heating reaction is 60° C. to 150° C.

In an embodiment of the disclosure, heating reaction time is 30 minutes to 5 hours.

The filter material provided by the disclosure is manufactured through the manufacturing method as described above and is configured to filter out white blood cells in the blood.

In view of the above, the invention provides a filter material and a manufacturing method thereof configured to filter out white blood cells in the blood, in which the supercritical carbon dioxide acts as the solvent, and the filter material is hydrophilized by using supercritical fluid processing technology, so that the problems of solvent recovery and wastewater treatment are effectively solved. In addition, the effect of solid-vapor separation of a solute can be achieved immediately after vaporization of supercritical carbon dioxide, so that unreacted solutes can be recovered, carbon dioxide can further be fully recovered for reuse. In another aspect, the supercritical fluid processing technology does not cause changes in fiber properties, which in turn enhances the effect of white blood cell filtration and shortens filtration time of the existing membrane materials.

To make the aforementioned more comprehensible, several embodiments are described in detail as follows.

DESCRIPTION OF THE EMBODIMENTS

In the specification, scopes represented by "a numerical value to another numerical value" are schematic representations in order to avoid listing all of the numerical values in the scopes in the specification. Therefore, the recitation of a specific numerical range covers any numerical value in the numerical range and a smaller numerical range defined by any numerical value in the numerical range, as is the case with any numerical value and a smaller numerical range thereof in the specification.

The disclosure provides a manufacturing method of a filter material, includes hydrophilizing the filter material by using supercritical fluid processing technology, so as to enable the blood to pass through a membrane material and to filter out white blood cells in the blood through selectivity (affinity) between the filter material and white blood cells. The manufacturing method of the filter material is described in detail as follows.

In the disclosure, the process of hydrophilizing the filter material by supercritical fluid processing technology includes the following steps. The filter material is placed in a cylinder and a hydrophilic agent is added. Next, carbon dioxide gas is poured into the cylinder through a pressure relief valve, the cylinder is placed in a glycerol tank, and a heating reaction is then performed. At the same time, a pressure of the cylinder is increased. After the reaction is over, the cylinder is taken out from the glycerol tank, the pressure relief valve is opened for pressure relief to lower a temperature and the pressure of the cylinder, and the filter material is taken out.

In the present embodiment, the hydrophilic agent may be added together with the filter material and may also be gradually added during the heating reaction process or during the process of pouring the carbon dioxide gas. In addition, the heating reaction may be performed when the carbon dioxide gas is poured or may be performed separately. As for the process of lowering the temperature and pressure of the cylinder, the temperature and pressure of the cylinder may be lowered at the same time or may be lowered separately.

In the present embodiment, the filter material may include a polyester compound base material, and the polyester compound base material may include, for example, polybutylene terephthalate. The hydrophilic agent may include, for example, polyether ester. Nevertheless, the disclosure should not be construed as being limited thereto, and other conventional polyester compound base materials or hydrophilic agents may also be included. The hydrophilic agent is added in an amount of, for example, 0.1 wt % to 10 wt % based on a total weight of the filter material. A bath ratio obtained by a weight of the filter material divided by a volume of the cylinder is, for example, 0.01 to 1. The pressure of the cylinder is 70 bar to 500 bar when the heating reaction is performed, and an amount of carbon dioxide added can be controlled by pressure. A temperature of the heating reaction is, for example, 60° C. to 150° C., and heating reaction time is, for example, 30 minutes to 5 hours.

The filter material provided by the disclosure is manufactured through the manufacturing method as described above. In the disclosure, supercritical carbon dioxide is mainly used as a solvent, and the filter material is hydrophilized through supercritical fluid processing technology to replace the grafting method or coating method of the prior art. Therefore, the problems of solvent recovery and wastewater treatment can be effectively solved. In addition, the supercritical fluid processing technology does not cause changes in fiber properties, which in turn enhances the effect of white blood cell filtration and shortens filtration time required by existing membrane materials.

The filter material and the manufacturing method thereof provided in the foregoing embodiments are described in detailed through experimental examples provided below. However, the experimental examples below are not intended to limit the disclosure.

EXPERIMENTAL EXAMPLES

The following experimental examples are provided to prove that the filter material manufactured by the manufacturing method provided by the disclosure exhibit a favorable property of filtering out white blood cells.

Note that since detailed description of the manufacturing method of the filter material is provided in the foregoing, preparation of the filter material is not to be described in detail below to simplify the description.

Preparation of Filter Material

Example 1, Example 2, Example 3

Conditions of supercritical fluid processing of Example 1, Example 2, and Example 3 are basically identical, and differences therebetween are conditions related to filtered blood samples and fluid flow velocities. The conditions of supercritical fluid processing of Example 1, Example 2, and Example 3 are provided as follows. A base material amount (bath ratio=base material weight/cylinder volume) is 0.27, an hydrophilic agent additive amount is 1%/to membrane material weight, the pressure of the cylinder is 285 bar, a reaction temperature is 120° C., and reaction time is 1.5 hours.

Comparative Example 1, Comparative Example 2, Comparative Example 3, Comparative Example 4

Both the filter materials in Comparative Example 1 and Comparative Example 2 are manufactured through the conventional coating method. As regards the conditions of supercritical fluid processing of Comparative Example 3, except the hydrophilic agent additive amount which is 0.05%/to membrane material weight, the rest of the processing conditions of Comparative Example 3 are identical to those of Example 1, Example 2, and Example 3. As for the conditions of supercritical fluid processing of Comparative Example 4, except the reaction temperature which is 50° C., the rest of the processing conditions of Comparative Example 4 are identical to those of Example 1, Example 2, and Example 3.

In Example 1, Example 2, and Example 3 and Comparative Example 1, Comparative Example 2, Comparative Example 3, and Comparative Example 4, white blood cells in the blood are filtered out, and the obtained experimental results are provided in the following Table 1. Based on the following Table 1, it can be seen that the filter material provided by the disclosure is capable of effectively filtering out white blood cells in the blood.

TABLE 1

| | Blood Sample Conditions | | Fluid Flowing Conditions | | Filtering Property of White Blood Cells | | |
|---|---|---|---|---|---|---|---|
| | Storage Time (hours) | Storage Condition | Filtering Time (min) | Flow Velocity (ml/min) | Filtering Property (log) | Residue (unit) | Solvent in Use |
| Example 1 | 6 | room temperature | 24 | 22.9 | 3.48 | $8.00 \times 10^5$ | $CO_2$ |
| Example 2 | 6 | room temperature | 36 | 13.2 | 3.63 | $2.00 \times 10^5$ | $CO_2$ |
| Example 3 | 6 | room temperature | 28 | 21 | 3.87 | $3.00 \times 10^5$ | $CO_2$ |
| Comparative Example 1 | 6 | room temperature | 16 | 25 | 3.95 | $2.00 \times 10^5$ | alcohol |
| Comparative Example 2 | 6 | room temperature | 21 | 25 | 3.92 | $2.00 \times 10^5$ | alcohol |
| Comparative Example 3 | 6 | room temperature | unable to filter | | | | $CO_2$ |
| Comparative Example 4 | 6 | room temperature | unable to filter | | | | $CO_2$ |

In view of the foregoing, the invention provides a filter material and a manufacturing method thereof configured to filter out white blood cells in the blood, in which supercritical carbon dioxide acts as the solvent, and the filter material is hydrophilized by using supercritical fluid processing technology to replace the conventional grafting method or coating method. Since the manufacturing method provided by the disclosure does not need to use a large amount of solvent (e.g., ethanol) to dissolve a hydrophilic monomer or a hydrophilic polymer, the problems of solvent recovery and wastewater treatment can be effectively solved. In addition, the effect of solid-vapor separation of a solute can be achieved immediately after vaporization of supercritical carbon dioxide, so that unreacted solutes may be recovered, carbon dioxide may further be fully recovered for reuse. In another aspect, supercritical fluid processing technology does not cause changes in fiber properties (e.g., fiber becomes thicker and a pore diameter of the filter material reduces), so that the filtering effect of white blood cells is enhanced and filtration time required by existing membrane materials is decreased.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A treatment method of a filter material, comprising using supercritical carbon dioxide as a solvent and hydrophilizing the filter material by using a supercritical fluid processing technology, so as to filter out white blood cells in blood,
    wherein a process of hydrophilizing the filter material by using the supercritical fluid processing technology comprises:
    placing the filter material in a cylinder and adding a hydrophilic agent;
    pouring carbon dioxide gas into the cylinder, performing a heating reaction to the cylinder, and increasing a pressure of the cylinder; and
    lowering a temperature and the pressure of the cylinder after the heating reaction is over and taking out the filter material,
    wherein the hydrophilic agent is added in an amount of 0.1 wt % to 10 wt % based on a total weight of the filter material.

2. The treatment method of the filter material of claim 1, wherein the filter material comprises a polyester compound base material.

3. The treatment method of the filter material of claim 1, wherein a bath ratio obtained by a weight of the filter material divided by a volume of fluid in the cylinder is 0.01 to 1.

4. The treatment method of the filter material of claim 1, wherein the pressure of the cylinder is 70 bar to 500 bar when the heating reaction is performed.

5. The treatment method of the filter material of claim 1, wherein a temperature of the heating reaction is 60° C. to 150° C.

6. The treatment method of the filter material of claim 1, wherein heating reaction time is 30 minutes to 5 hours.

\* \* \* \* \*